United States Patent
Curran et al.

(10) Patent No.: US 9,776,182 B2
(45) Date of Patent: Oct. 3, 2017

(54) HANDLING LIQUID SAMPLES

(71) Applicant: GenCell Biosystems Ltd., Raheen, County Limerick (IE)

(72) Inventors: Kieran Curran, Ballyclough (IE); David McGuire, Enniscorthy (IE); Brian Chawke, Askeaton (IE); Paul Fleming, Castleroy (IE); Brian Barrett, Cashel (IE); Noel Sirr, Ballymoe (IE)

(73) Assignee: GenCell Biosystems Ltd., Raheen, County Limerick (IE)

( * ) Notice: Subject to any disclaimer, the term of this patent is extended or adjusted under 35 U.S.C. 154(b) by 0 days.

(21) Appl. No.: 14/426,683

(22) PCT Filed: Nov. 26, 2013

(86) PCT No.: PCT/IB2013/003145
§ 371 (c)(1),
(2) Date: Mar. 6, 2015

(87) PCT Pub. No.: WO2014/083435
PCT Pub. Date: Jun. 5, 2014

(65) Prior Publication Data
US 2015/0283541 A1 Oct. 8, 2015

Related U.S. Application Data

(60) Provisional application No. 61/730,336, filed on Nov. 27, 2012.

(51) Int. Cl.
*B01L 3/00* (2006.01)
*B01L 3/02* (2006.01)
(Continued)

(52) U.S. Cl.
CPC ............... *B01L 3/502* (2013.01); *B01L 3/022* (2013.01); *B01L 3/50851* (2013.01); *B01L 7/00* (2013.01);
(Continued)

(58) Field of Classification Search
None
See application file for complete search history.

(56) References Cited

U.S. PATENT DOCUMENTS

| 3,783,696 A | 1/1974 | Coleman |
| 3,952,599 A | 4/1976 | Ayres |

(Continued)

FOREIGN PATENT DOCUMENTS

| CN | 1369698 A | 9/2002 |
| CN | 101028607 A | 9/2007 |

(Continued)

OTHER PUBLICATIONS

Lee et al. "On-chip procedures for magnetic particle-based assay in droplets", 16th International Conference on Miniaturized Systems for Chemistry and Life Sciences, Oct. 28-Nov. 1, 2012, Okinawa, Japan, pp. 347-349.

(Continued)

*Primary Examiner* — Betty Forman
(74) *Attorney, Agent, or Firm* — Bret E. Field; Bozicevic, Field & Francis LLP

(57) ABSTRACT

Devices, systems and methods for making and handling liquid samples are disclosed.

12 Claims, 5 Drawing Sheets

(51) Int. Cl.
  *B01L 7/00* (2006.01)
  *C12Q 1/68* (2006.01)
(52) U.S. Cl.
  CPC .............. *B01L 7/52* (2013.01); *C12Q 1/6806* (2013.01); *B01L 2200/0605* (2013.01); *B01L 2200/0673* (2013.01); *B01L 2200/0684* (2013.01); *B01L 2300/0829* (2013.01); *B01L 2300/0838* (2013.01); *B01L 2300/12* (2013.01); *B01L 2300/161* (2013.01); *B01L 2300/1827* (2013.01); *B01L 2300/1883* (2013.01); *B01L 2300/1894* (2013.01); *B01L 2400/0406* (2013.01); *B01L 2400/0487* (2013.01)

(56) References Cited

U.S. PATENT DOCUMENTS

| | | | |
|---|---|---|---|
| 4,962,395 A | | 10/1990 | Baird |
| 5,059,398 A | | 10/1991 | Kenney |
| 5,221,518 A | | 6/1993 | Mills |
| 5,408,306 A | | 4/1995 | Anderson |
| 5,474,796 A | * | 12/1995 | Brennan .............. B01J 19/0046 422/547 |
| 5,486,337 A | * | 1/1996 | Ohkawa .............. B01F 13/0071 239/690 |
| 5,505,877 A | | 4/1996 | Krivohlavek |
| 5,639,426 A | | 6/1997 | Kerr et al. |
| 5,980,936 A | | 11/1999 | Krafft et al. |
| 6,136,609 A | | 10/2000 | Sato et al. |
| 6,284,546 B1 | | 9/2001 | Bryning et al. |
| 6,326,211 B1 | | 12/2001 | Anderson et al. |
| 6,640,891 B1 | | 11/2003 | Oldenburg |
| 7,129,091 B2 | | 10/2006 | Ismagilov et al. |
| 7,138,233 B2 | | 11/2006 | Griffiths et al. |
| 7,238,323 B2 | | 7/2007 | Knapp et al. |
| 7,244,396 B2 | | 7/2007 | Chait et al. |
| 7,244,567 B2 | | 7/2007 | Chen et al. |
| 7,252,943 B2 | | 8/2007 | Griffiths et al. |
| 7,323,305 B2 | | 1/2008 | Leamon et al. |
| 7,329,545 B2 | | 2/2008 | Pamula et al. |
| 7,439,014 B2 | | 10/2008 | Pamula et al. |
| 7,582,446 B2 | | 9/2009 | Griffiths et al. |
| 7,597,809 B1 | | 10/2009 | Roberts |
| 7,638,276 B2 | | 12/2009 | Griffiths et al. |
| 7,759,132 B2 | | 7/2010 | Pollack et al. |
| 7,776,927 B2 | | 8/2010 | Chu et al. |
| 7,842,457 B2 | | 11/2010 | Berka et al. |
| 7,901,939 B2 | | 3/2011 | Ismagilov et al. |
| 7,915,013 B2 | | 3/2011 | Cho et al. |
| 7,943,348 B2 | | 5/2011 | Cho et al. |
| 8,029,744 B2 | | 10/2011 | Noda et al. |
| 8,128,798 B2 | | 3/2012 | Adachi et al. |
| 8,158,359 B2 | | 4/2012 | Leamon et al. |
| 8,252,539 B2 | | 8/2012 | Quake et al. |
| 8,256,308 B2 | | 9/2012 | Buechner |
| 8,263,023 B2 | | 9/2012 | Le Vot et al. |
| 8,273,573 B2 | | 9/2012 | Ismagilov et al. |
| 8,304,193 B2 | | 11/2012 | Ismagilov et al. |
| 8,329,407 B2 | | 12/2012 | Ismagilov et al. |
| 8,367,326 B2 | | 2/2013 | Griffiths et al. |
| 8,709,762 B2 | | 4/2014 | Hindson |
| 8,748,102 B2 | | 6/2014 | Berka et al. |
| 8,765,380 B2 | | 7/2014 | Berka et al. |
| 8,790,876 B2 | | 7/2014 | Leamon et al. |
| 9,194,772 B2 | | 11/2015 | Lee et al. |
| 9,277,759 B2 | | 3/2016 | Bibette et al. |
| 2002/0009392 A1 | | 1/2002 | Wolk et al. |
| 2002/0114740 A1 | | 8/2002 | Yamamoto |
| 2003/0032198 A1 | * | 2/2003 | Lugmair .............. B01L 3/0268 436/180 |
| 2004/0203174 A1 | | 10/2004 | Jones et al. |
| 2005/0087122 A1 | | 4/2005 | Ismagilov et al. |
| 2005/0221370 A1 | | 10/2005 | Hodge |
| 2006/0246224 A1 | | 11/2006 | Neitzel |
| 2007/0026421 A1 | | 2/2007 | Sundberg et al. |
| 2007/0037294 A1 | | 2/2007 | Pamula et al. |
| 2007/0042367 A1 | | 2/2007 | Tao et al. |
| 2007/0243634 A1 | | 10/2007 | Pamula et al. |
| 2007/0275415 A1 | | 11/2007 | Srinivasan et al. |
| 2008/0023330 A1 | | 1/2008 | Viovy et al. |
| 2008/0224086 A1 | | 9/2008 | Falkowski et al. |
| 2009/0023189 A1 | | 1/2009 | Lau et al. |
| 2009/0131543 A1 | | 5/2009 | Weitz et al. |
| 2009/0260458 A1 | | 10/2009 | Joseph et al. |
| 2010/0015614 A1 | | 1/2010 | Beer et al. |
| 2010/0016452 A1 | | 1/2010 | Nedwed et al. |
| 2010/0022414 A1 | | 1/2010 | Link et al. |
| 2010/0096342 A1 | | 4/2010 | Roberts |
| 2010/0105112 A1 | | 4/2010 | Holtze et al. |
| 2010/0120635 A1 | | 5/2010 | Davies et al. |
| 2010/0173394 A1 | | 7/2010 | Colston, Jr. et al. |
| 2010/0267585 A1 | | 10/2010 | Terbrueggen |
| 2011/0171748 A1 | | 7/2011 | Cox et al. |
| 2011/0212516 A1 | | 9/2011 | Ness et al. |
| 2012/0028342 A1 | | 2/2012 | Ismagilov et al. |
| 2012/0208241 A1 | | 8/2012 | Link |
| 2012/0276543 A1 | | 11/2012 | Quake et al. |
| 2012/0276544 A1 | | 11/2012 | Quake et al. |
| 2012/0298205 A1 | | 11/2012 | Schertzer et al. |
| 2013/0109575 A1 | | 5/2013 | Kleinschmidt et al. |
| 2013/0190189 A1 | | 7/2013 | Griffiths et al. |
| 2014/0113300 A1 | | 4/2014 | Samuels |
| 2014/0162885 A1 | | 6/2014 | Berka et al. |
| 2014/0199730 A1 | | 7/2014 | Agresti et al. |
| 2014/0199731 A1 | | 7/2014 | Agresti et al. |

FOREIGN PATENT DOCUMENTS

| | | |
|---|---|---|
| CN | 102316989 A | 1/2012 |
| DE | 10039195 A1 | 2/2002 |
| EP | 1019496 B1 | 7/2000 |
| EP | 1053784 A2 | 11/2000 |
| EP | 0892035 B1 | 10/2004 |
| EP | 1485204 B1 | 2/2006 |
| EP | 1496120 B1 | 3/2007 |
| EP | 1482036 B1 | 10/2007 |
| EP | 1508044 B1 | 9/2010 |
| EP | 1801214 B1 | 11/2010 |
| EP | 2258846 A2 | 12/2010 |
| EP | 2278337 A2 | 1/2011 |
| EP | 2248578 B1 | 6/2012 |
| EP | 1908832 B1 | 12/2012 |
| EP | 2703497 A1 | 3/2014 |
| JP | 2008538077 A | 10/2008 |
| JP | 2009534653 A | 9/2009 |
| JP | 2010503516 A | 2/2010 |
| WO | WO 93/03151 A1 | 2/1993 |
| WO | WO 94/08759 A1 | 4/1994 |
| WO | WO 2004/038363 A2 | 5/2004 |
| WO | WO 2004069413 A1 | 8/2004 |
| WO | WO 2005/002730 A1 | 1/2005 |
| WO | WO 2007/024778 A2 | 3/2007 |
| WO | WO 2007/024798 A2 | 3/2007 |
| WO | WO 2007/024800 A2 | 3/2007 |
| WO | WO 2007/024914 A2 | 3/2007 |
| WO | WO 2007/120241 A2 | 10/2007 |
| WO | WO 2008/130623 A1 | 10/2008 |
| WO | WO 2008/144288 A1 | 11/2008 |
| WO | WO 2009/061372 A1 | 5/2009 |
| WO | WO 2009/134395 A1 | 11/2009 |
| WO | WO 2009/149257 A1 | 12/2009 |
| WO | WO 2010/063937 A1 | 6/2010 |
| WO | WO 2010/104604 A1 | 9/2010 |
| WO | WO 2010/121307 A1 | 10/2010 |
| WO | WO 2012/011091 A2 | 1/2012 |
| WO | WO 2012/024658 A2 | 2/2012 |
| WO | WO 2013/111016 A2 | 8/2013 |
| WO | WO 2013/192351 A1 | 12/2013 |
| WO | WO 2014/039587 A1 | 3/2014 |

(56) References Cited

FOREIGN PATENT DOCUMENTS

WO    WO 2014/093714 A1    6/2014
WO    WO 2014/207577 A2    12/2014

OTHER PUBLICATIONS

Lehmann et al. "A Lab-on-a-Chip using magnetic droplets", NSTI-Nanotech 2006, vol. 2, 2006, pp. 477-480.
Mastrobattista et al. "High-throughput screening of enzyme libraries: in vitro evolution of a beta-galactosidase by fluorescence-activated sorting of double emulsions", Chem Biol. Dec. 12, 2005(12):1291-300.
Tawfik et al. "Man-made cell-like compartments for molecular evolution", Nat. Biotechnol. Jul. 1998; 16(7):652-6.
Utada et al. "Monodisperse Double Emulsions Generated from a Microcapillary Device", Science, Apr. 22, 2005, vol. 308, No. 5721, pp. 537-541.
Wu et al. "A double-emulsion microfluidic platform for in vitro green fluorescent protein expression", 2011 J. Micromech. Microeng. 21 054032, 7 pages.
Meldrum et al. "Automation for Genomics, Part One: Preparation and Sequencing", Genome Research 10, pp. 1081-1092 (2000).

\* cited by examiner

HANDLING LIQUID SAMPLES

RELATED APPLICATIONS

This application claims the benefit of U.S. Provisional Application Ser. No. 61/730,336 filed 27 Nov. 2012, which is incorporated herein by reference in its entirety.

BACKGROUND

Currently the processing of biological samples has a number of key drawbacks. These include the requirement for relatively large volume reaction volumes—resulting in high reagent costs; high consumable costs; and labour-intensive protocols and processes, which are highly susceptible to cross-contamination. For these reasons complete control and isolation of each individual sample within the biochemistry process cannot currently be ensured.

For a number of biochemistry process applications—cell screening, immunoassays, nucleic/ribonucleic acid sample extractions, nucleic acid isolation/purifications, nucleic acid amplifications, nucleic acid library preparation for sequencing—and not limited to these, the limitations of volume size, chemistry cost, consumable cost, labour cost, and the reaction efficiency are evident.

In pharmaceutical research and development, compound screening can be used evaluate the effect of target drugs on cell populations. Cells are combined in solution with the target compound-of-interest with the option to include a chemical stimulus to acceleration interaction. Cells are typically exposed to the compound for up to 48 hrs and then analysed to test for certain cell protein expressions (eg. Cytokine measurement) and/or profiled for gene expression via RT-PCR. Currently, this type of testing typically takes place in 96/384 well plate types requiring up to 1.5 milliliters of cells in suspension.

Nucleic acid sample extraction and purification/isolation are steps that are typically required to liberate and isolate genetic material from cellular content (e.g. a blood or tissue sample). This requires cells to be suspended in an excess of buffer to perform lysis that breaks down cell walls to expose nucleic acid. Depending on sample type/origin, nucleic acid may be required to be purified to reduce/eliminate interfering compounds that affect further analysis. Typical approaches to performing nucleic acid purification involve centrifuging through membranes/columns to promote DNA binding followed by re-suspension in suitable buffer for further analysis. Another common method is to introduce magnetic bead suspensions to which nuclei acid may bind. The action of a magnetic field can then be used to immobilize beads while inhibiting content is removed. A suitable buffer is then typically used to re-suspend nucleic acid of interest to yield analysis-ready sample without inhibiting compounds. This process is typically performed in 96-well or 384-well plates requiring tens of microliters of starting sample.

Library preparation is a process by which genomic nucleic acid is prepared for analysis via next generation sequencing. At present, next-generation platforms use slightly different methodologies such as pyrosequencing, sequencing by synthesis or sequencing by ligation. Most platforms, however, require nucleic acid preparations prior to sequencing. Typical steps include fragmentation (sonication, nebulization or shearing), followed by DNA repair and end polishing (blunt end or A overhang) and, finally, platform-specific adaptor ligation. Even for today's state-of-the-art sequencers a relatively high local concentration of the target molecule is required to sequence accurately. To streamline a particular workflow, automated machinery must overcome the challenges associated with automating and miniaturizing a series of processes aimed at modifying and amplifying nucleic acid content. This biochemistry process is generally performed in 96 or 384 static well plates with typical volumes ranging from 10 microliters to 200 microliters.

Another biochemistry process, pyrosequencing, mixes a relatively high concentration of nucleic acid with primer-coated beads. The nucleic acids attach and form a clonal colony on the beads. This is then amplified using emulsion-based PCR. The sequencing machine contains a large number of picoliter-volume wells that are large enough for a single bead along with the relevant enzymes required for sequencing. Pyrosequencing uses the luciferase enzyme to generate light as read-out, and the sequencing machine takes a picture of the wells for every added nucleotide. One of the key difficulties in this process is the efficient coating of the beads with primers. A percentage of beads using current technologies are not properly coated with primer chemistry, resulting in poorer reaction efficiencies. Using today's technologies to improve the coating efficiencies of the beads would require an unsustainable increase in reagent cost.

Within nucleic acid ligation similar biochemistry processing issues arise. Nucleic acid ligation has become an important tool in modern molecular biology research for generating recombinant nucleic acid sequences. For example, nucleic acid ligases are used with restriction enzymes to insert nucleic acid fragments, often genes, into plasmids for use in genetic engineering. Nucleic acid ligation is a relatively common technique in molecular biology wherein short strands of DNA may be joined together by the action of an enzyme, ligase, at a specific temperature, commonly 16-25° C. depending on the protocol used. To join more than two sequences of short DNA strands together, for example, in the construction of a synthetic genetic sequence, it is impossible to combine all the DNA strands and then perform the ligation. This would result in random sequences in which the end of one strand would be joined to the start of an incorrect strand. This incorrect sequence, or orientation, would not be desirable in a synthetically-constructed gene where the order of the genetic code is crucial. To perform the technique correctly pairwise combinations of neighbouring sequences must first be ligatated to yield the correct orientation. These paired synthetic constructs may then be ligated in the correct orientation to yield even longer synthetic constructs. The process involves a large and intricate amount of chemistry processing and manipulation. This can be quite a labour intensive process or if performed using today's liquid handling and results in large consumable costs and suffers from the known dead volume losses of the static well plates and pipette aspirations. Also using today's liquid handling technologies the mixing and control of small volumes is limited by the ability to aspirate and manipulate relatively small volumes. Typical volumes used in nucleic acid ligation are 10-200 microliters with nucleic acid strand lengths between 50-200 base pairs.

Polymerase Chain Reaction (PCR) has been used extensively to amplify targeted DNA and cDNA for many applications in molecular biology. The PCR technique amplifies a single or a few copies of a piece of DNA, generating thousands to billions of copies of a particular DNA sequence. Modern PCR instruments carry out the PCR process in reaction volumes ranging from 5-200 microliters. One of the largest obstacles to carrying out PCR in small volumes is the difficulty in manipulating small volumes of the constituent reagents with manual pipettes. The large volume size is a direct result of the poor capability of existing technologies to dispense and mix sub-microliter volumes. Furthermore, for the next generation microfluidic technologies based on flowing systems, these are still limited by the starting volume dispensed versus the actual amount of sample required for the biochemistry process. These microfluidic systems are also limited during the biochemistry process to a defined protocol control of the samples. These systems typically rely on micro-scale fluid channel networks to transport and mix sub-microliter volumes. Some of the major drawbacks of these technologies include: (1) the single use or limited use of the microfluidic consumable to prevent contamination; (2) the lack of dynamic control of the each individual sample, that is, the inability to transport and/or mix any individual sample at any point in the biochemistry process; and (3) the closed architecture of the system resulting in instrumentation being incapable of dealing with an occurrence of a bubble degassing from a reaction.

In particular, current methods of Digital Polymerase Chain Reaction (dPCR) are performed through the division of an initial sample into multiple smaller volumes samples until one DNA template remains in each subvolume. Counting the number of positive subvolumes which contain DNA, the starting copy number in the original volume can be calculated. Typically, this involves multiple serial dilution steps to generate a sample volume with statistically one DNA target per reaction volume. Statistically a subset of the total volume may be tested to determine the initial copy number, allowing for a reduction in the total number of PCR reactions. However, for rare target detection, a larger subset of volumes need to be tested to improve the statistical accuracy. This results in a larger number of blank volumes and a larger test volume—resulting in the use of more chemistry, time, instrumentation, sample handling, and processing steps.

Another method of dPCR is whereby an emulsion of the test volume is generated in an oil-based carrier. This method is an effort to reduce the number of instruments required and time required for a result. First, the target sample is diluted and emulsified into small enough volumes with a statistical distribution of less than one copy per droplet, within the carrier oil. This larger volume can then be treated as a single sample volume and processed using PCR protocols. However this method is generally limited to end point detection. Further instrumentation is required in the form of a flow cytometer, thereby being able to detect the target presence per droplet flowing past a sensor. Flow cytometers are typically expensive; can require specific fluid mediums and only allow for endpoint detection. The limitations of endpoint detection include the requirement of a post processing step; longer time to result; specificity and requirement for more instrumentation. A further challenge for emulsion based PCR methods is the stability required and control of each droplet. Droplet merging or splitting introduces further statistical errors into the processing.

Today's pipetting and liquid handling systems are unable to process 100% of the given starting volume for each of the applications discussed above. For pipettes both the liquid storage system—static plastic well plates—and the mechanical actuation within the system prevent complete aspiration of the sample. This loss or dead volume in static plates can be accounted for by the surface wetting characteristics and the geometry, neither of which current technologies can account for.

In flowing systems the collection of individual biological samples during—or at the end of the biochemistry process—is proving to be very challenging for existing technologies. Typical continuous flowing systems comprise of pumps and reservoirs which generally make the easy retrieval of critical fluids, particularly at the microscale, technically difficult. Also, within flowing systems initial priming of the system is time consuming, costly and if done incorrectly leads to a catastrophic failure of the test requiring a retest of the biological sample.

Another drawback to existing biochemistry processing is the inability to automate the biochemistry process for nanoliter and sub-nano-liter volumes. The transport, mixing or retrieval of each individual sample cannot be performed by existing automated technologies.

In more general chemistry processing, such as generic microchemistry, where the manipulation of small amounts of fluid is necessary, one can clearly see the limitations of current technology in the volume of waste fluid remaining in the static well plates or within the system. This is a result of current technology's lack of capability to dispense and control smaller volumes demanded by evermore sophisticated molecular biology techniques, and the call for improved efficiencies.

Genotyping is a widely used process for determining genetic variation between members of a species. Single nucleotide polymorphisms (SNPs) are a particular type of DNA sequence variation and the determination of SNPs can give an insight into the cause of a variety of diseases. SNPs are also useful for predicting phenotypic differences. SNP genotyping is a powerful tool in targeting specific subsets of SNPs which have been identified to give relevant phenotypic information. A variety of methods such as PCR and flap endonuclease assays are useful for the high throughput genotyping of SNPs but suffer from the limitations associated with standard liquid handling practices such as large reaction volumes and their associated cost and time required to thermal cycle, the dead volumes inherent with using SBS well plates, and consumable costs through using large amounts of well plates and tips.

The invention is, therefore, directed towards providing improved sample handling to overcome at least some of the above problems.

SUMMARY

Devices, systems and methods for making and handling liquid samples are disclosed. In particular, the invention addresses many of the problems described above by, for example, providing automation for library preparation; volume recoverability at each step; reduced sample handling volumes; reduced sample handling processes, i.e., reduced movement between plates for process steps; reduced usage of protocol reagents; a non-disposable, no-contamination platform for processing; a continuous flow of independent processing plates or chip; flexible protocol for each thermal chip or plate, i.e., the ability to independently program the thermal cycling and reagent protocol for different chips; easily scalable chip/plate technology to allow for high throughput; and the potential for a normalization step to standardize the number of nucleotide sequence copies in each sample.

DETAILED DESCRIPTION

Capillary Metering System

Figure 1:
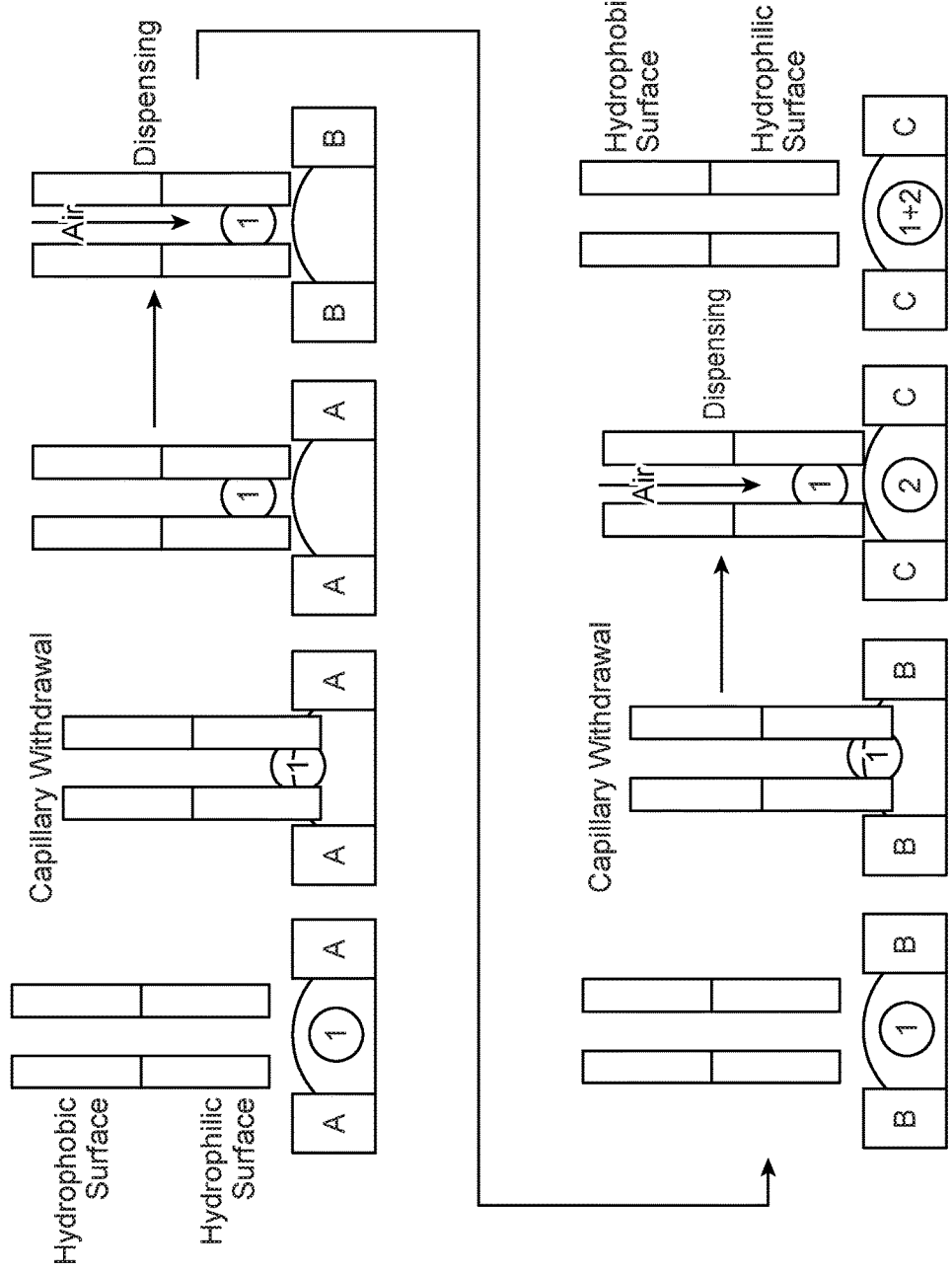
FIG. 1 schematically shows a capillary system.

A system for dispensing an aqueous liquid can be based on capillary action. Such a capillary system can include a capillary tube having an inner surface that defines the capillary, or lumen. The tube can also have an outer surface. The outer surface may be generally cylindrical, including the side, top and bottom. The inner surface can include two regions, a distal metering region and a proximal limiting region. The metering region of the inner surface may be substantially hydrophilic while the limiting region of the inner surface may be substantially hydrophobic. The entire outer surface may also be hydrophobic.

When an end, herein labelled the distal end, of the capillary tube is brought into contact with an aqueous sample, the sample is drawn by capillary action into the lumen. But the capillary action will only work to the extent that the aqueous sample is contained within a hydrophilic, i.e., wettable, section of the lumen. When enough aqueous sample has been drawn into the lumen that the metering region is entirely filled, capillary action will cease to draw in additional sample liquid, because no further wettable surface is available to the aqueous sample. In this way, the capillary action can be exploited to precisely meter a desired quantity of aqueous liquid. For a lumen of constant cross-sectional area, the volume of liquid drawn in by capillary action will be equal to the length of the metering section times the cross-sectional area of the lumen.

In some embodiments, the metering region and limiting region can be constructed as follows. A length of capillary tubing can be coated with, or formed entirely from, a hydrophobic polymer, for example a fluorocarbon polymer such as polytetrafluoroethylene (PTFE). An etching solution is then passed through the interior lumen of the tube, stripping the PTFE coating of fluorine atoms near the surface of the PTFE. Fluorine atoms are typically stripped down to a depth a few Angstroms by this process. The resulting etched PTFE surface is hydrophilic. The tube is then cleaned and cut to length to form a metering region having a desired internal volume. That internally etched, internally hydrophilic section of tubing is then attached to a section of hydrophobic tubing to form the entire capillary tube. In some embodiments polymers, such as polyimide, can be used to form the capillary tube.

In some embodiments, the capillary tube is formed of a glass substrate. Glass is naturally hydrophilic, so where the substrate is glass, instead of, for example, a naturally hydrophobic polymer, no surface treatment is necessary to form the metering region. The outer surface and limiting region may be formed by coating the glass with a hydrophobic material, such as the polymers mentioned above.

One benefit of making the outer surface of the tube, especially the distal end of the tube, hydrophobic is that the aqueous sample will not cling to such material. Thus the hydrophobic outer surface protects the system from contaminating one aqueous liquid sample with droplets from a different aqueous sample. Inserting the distal end of the tube into an aqueous sample will results in liquid drawn into the hydrophilic metering region, but not clinging to the hydrophobic region.

In addition to a capillary tube, a capillary system can also include a pressure source in fluid communication with the proximal end of the tube. The pressure source can provide positive air pressure, or could use another gas or liquid, but air is preferred. Application of the positive pressure can be used to drive an aqueous sample out of the capillary. The lowest positive air pressure is found at which the aqueous is completely driven out of the capillary and there after must be accurately and precisely controlled. The positive pressure must be evenly distributed when there are multiple capillaries used in parallel. The shortest time is found for the positive pressure to be applied to the capillary to allow all the aqueous sample to be driven out and the pressure neutralised immediately to prevent air being blown out through the capillary once the aqueous has been driven out of the capillary. The positive pressure and time applied must then be used to carry out sample dispense testing where the sample volume accuracy and precision, sample breakup and disturbance to the CLC are investigated. The positive pressure and time are then adjusted to obtain the optimum sample dispense to CLC within these parameters. The system can also include a capillary controller programmed to apply the positive pressure at a desired time so that the aqueous sample is dispensed at a predetermined location. The location could be, for example, a stabilization site for a composite liquid cell, where an aliquot of encapsulating fluid could be ready to receive the aqueous sample. It should be noted that, while positive pressure can be used to drive the aqueous liquid out of the lumen, no negative pressure is needed to draw the liquid into the lumen because the liquid is drawn in by capillary action.

In one embodiment following a post aqueous sample dispense a procedure to ensure all remaining sample is removed from the capillary tube and the capillary is washed and dried ready for the next aqueous sample aspirate and dispense cycle. The capillary is moved from the dispense location and lowered into a negative pressure air flow where a high positive pressure is blown through the capillary to ensure complete evacuation of aqueous from the internal cavity of the capillary. The negative air flow captures any remaining aqueous sample being blown out and also dries the outer surfaces of the capillary. The negative air flow is then filtered to contain any contaminants which could otherwise become airborne. Wash solutions are then aspirated by the capillary from a reservoir and dispensed into the negative pressure air flow to ensure decontamination of the capillary.

Figure 2:
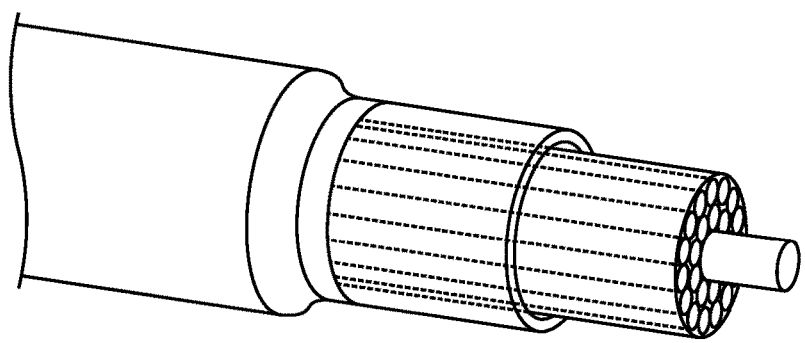
FIG. 2 is a photograph of a capillary system including an air sheath.

FIGS. 1 and 2 show exemplary embodiments of such a system.

The capillary system can also include an air sheath, which consists of an externally applied air flow to the capillary tube. The externally applied air flow reduces the likelihood that an aqueous sample will attach to any external hydrophilic region.

The capillary system can also include an actuator to move the capillary tube between locations. The actuator can be controlled by the capillary controller, which can be programmed to cause the actuator to move the tube. A typical program might first move the distal end of the tube into contact with an aqueous sample so as to draw the aqueous sample into the tube, then move the capillary tube so that the distal end is adjacent to a dispensing location such as a stabilizing feature or an existing composite liquid cell (hereinafter "CLC"), and finally apply sufficient positive pressure to the proximal end of the tube to eject the aqueous sample from the distal end of the tube.

In one particular embodiment, the internal diameter of the capillary tube is about 200 to 250 m, preferably 221 or 230 m, and the outer diameter is about 800 m. Any volume of aqueous solution can be chosen to be drawn into the system. Particular capillary tubes may be designed to draw in from about 10 nanoliters to about 10000 nanoliters, an in particular about 500 nanoliters.

In another embodiment, for multiple capillary metering from a single controller—multiple capillary tubes with the inner surface consisting of a single distal metering region are arranged within a cavity, thereby providing a limiting region.

In another embodiment the pressure controller variably controls the capillary metering volume. The treated tube is cut to a given length and based on the radius of that tube this then gives a set maximum volume. The volume within distal metering region is controlled using air pressure within the assembly. The air pressure is used to dispense however in this embodiment a controlled constant pressure is maintained within the capillary tube—thereby providing a volume control within the hydrophilic distal metering region. This is achieved by balancing the pressure force against the capillary force for a given volume. The fluid will capillary to a height that is matched by pressure force. Change the pressure and the volume is changed. This is all within the total capillary height for a given fluid and tube radius.

In another embodiment, a capillary metering system can include a plurality of capillary tubes. The proximal ends of all the capillaries can be in fluid communication with a single pressure conduit, and the pressure conduit in fluid communication with the pressure source. In this way, a single pressure source can be used to apply a single positive pressure to simultaneously dispense liquid from all of the plurality of capillary tubes. Similarly, a single pressure source can apply a single positive pressure to balance the capillary force in all of the plurality of capillary tubes.

Reusable CLC Plate

As explained previously, CLCs are useful environments for carrying out biological sample processing, such as fragmentation and bar-coding, nucleic acid amplification, and detection of target nucleic acids. Such processing, whether carried out in a CLC, or in a well in a disposable tray, typically requires precise thermal control of the sample, as well as the ability to add and remove liquids such as reagents. Whether a disposable tray is used or not, the system must include some mechanism for altering the environment of the sample as the sample progresses through the process. Historically, this has sometimes involved transferring samples from one container to another with the attendant risk of contamination, or moving a closed container from one place to another in order to expose the sample to activities associated with a particular location with the attendant mechanical complications. Such systems typically use disposable plates to reduce contamination. But disposable plates have drawbacks, for example, every disposable used has a cost to the consumer. A reusable plate that does not introduce contamination problems can address these concerns.

A device such as a reusable plate can be used in a system for processing a sample contained in a CLC. The plate/device can include a base or vessel portion, sized and shaped to contain a bath of carrier liquid. The carrier liquid may have a free surface on which CLCs may be formed. The vessel can be highly thermally conductive, e.g., composites, ceramics, and metals, in particular, aluminium, so that heat applied to the vessel will be spread evenly through the carrier liquid and into the CLCs. The plate can include a cooling region configured to be operably attached to either a thermoelectric module, a fluidic cooling system or a forced convection cooling system. The plate can also include a heating element in thermal contact with the vessel. The heating element could be, for example, an etched foil heater electrically connected to a controller, the controller being programmed to activate the heating element to generate a desired thermocycle in the CLCs. The plate can also include a tray with stabilization features configured to stabilize a CLC on the free surface of the carrier liquid. In some embodiments, the plate can include an inlet for supplying carrier fluid to the vessel in order to replenish carrier liquid that may have evaporated during use.

Alternatively, the heating element could be an electrical wire, activated by passing an electrical current through the wire. The wire can be electrically insulated with a material, for example, PTFE, that can also be used to form the stabilization features. In this embodiment, the heating element need not be in direct thermal contact with the vessel; the heat will be more directly transferred to the CLCs through the electrically insulating stabilization features. The stabilization features can be integral with the wire's insulation, and can be formed of the same material. Alternatively, the stabilization features can be attached to the wire, and/or possibly made of a different material than the insulation. Such an embodiment may or may not also include a tray comprising the stabilization features. The heating element can be incorporated into the tray or can be provided as a separate element of the plate.

CLCs can be formed on such a reusable plate, after which processing of the sample liquid in the CLCs can take place without ever moving the CLC from its location on the plate. In some embodiments, such a plate is moved through a larger sample processing system without ever displacing the CLC or exposing the sample liquid from inside the encapsulating liquid. This has obvious benefits for reducing contamination when compared to any process that allows the sample liquid to be exposed. The encapsulation of the composite liquid cells avoids contact of the sample with the plate, allowing the plate to be reused without fear of contamination and without the cost of replacing the plate after every run. Incorporation of the heating element into the plate allows for precise control of the temperature in the sample liquid. This particular combination of elements has a wide variety of benefits.

Figure 3:
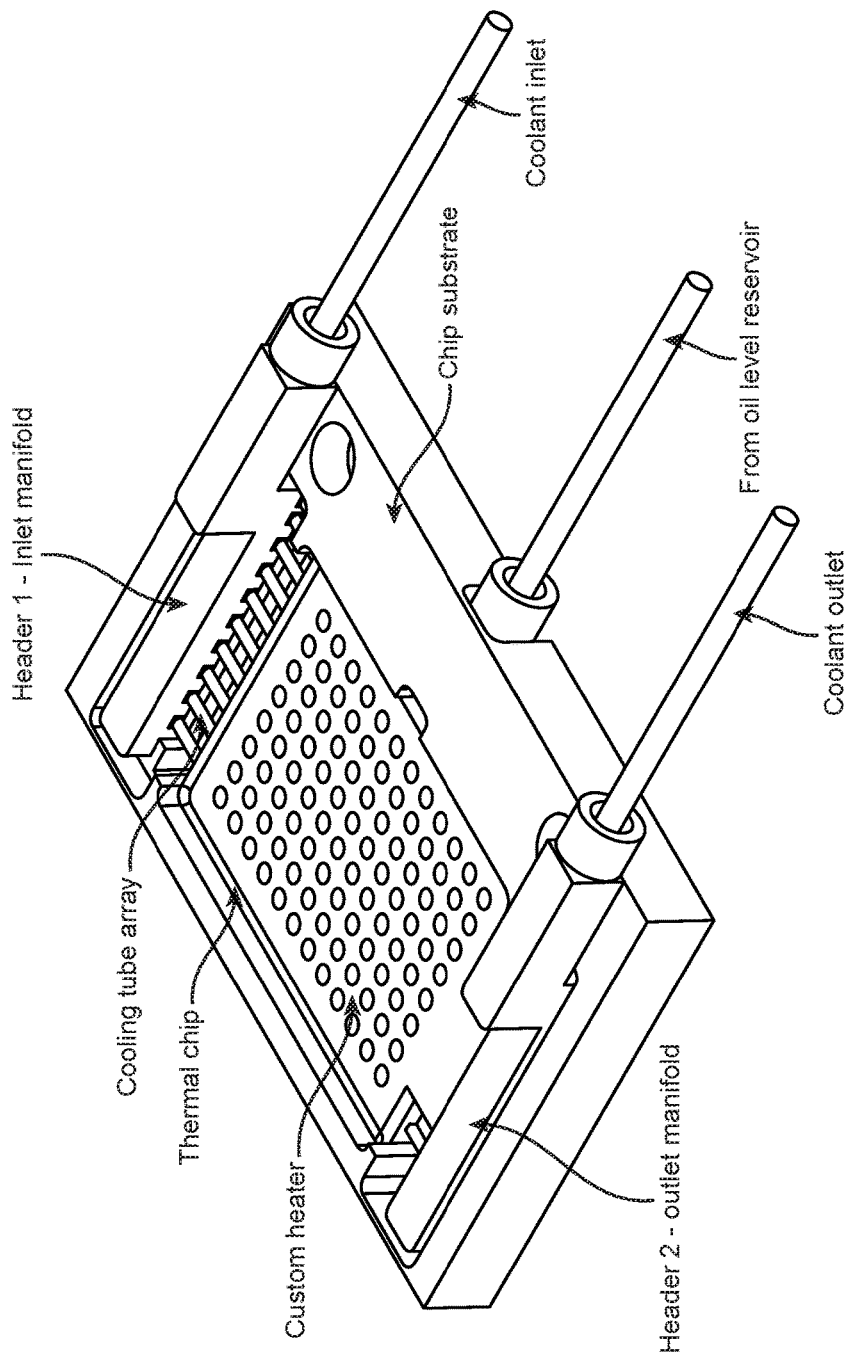
FIG. 3 schematically shows one embodiment of a reusable plate.

One example of such a plate is schematically shown in FIG. 3. Other arrangements of the elements are possible as well. In some cases it may be beneficial to locate the heating element as close as possible to the stabilization features where the CLCs are typically located. Since it is the temperature of the samples within the CLCs that should be controlled, locating the heating element as close to the CLCs as possible can reduce energy consumption and increase efficiency, while also reducing evaporation of the carrier liquid.

The plate can also be arranged to allow direct line of sight inspection of fluorescence emanating from the vicinity of each stabilization feature. Where the processing of the CLCs includes inferring the presence of a target nucleotide sequence based on detection of fluorescence or some other electromagnetic observation or interrogation, it can be useful to maintain a clear line of sight from a detector to each stabilization feature where a CLC may be housed.

The plate can be configured to allow for through CLC optical interrogation, wherein a line of sight from a detector to a CLC is maintained through the plate. Optical detection methods include but are not limited to fluorescence, absorbance, Raman, interferometry and shadow-graphy.

The plate can also include a lid sized and shaped to mate with the vessel so as to enclose the CLCs and stabilization features with the plate. The lid may be openable and closeable by an automatic actuator, or may be manually operated. The lid can seal the carrier liquid into the vessel in order to inhibit evaporation of the carrier liquid. The lid can partially seal against the vessel, or it can be substantially airtight, maintaining a pressure seal. The lid can be transparent to any particularly desired wavelength of light, to allow for electromagnetic interrogation of the CLCs. A heating element can be included in the lid.

The plate can be used to handle samples in CLCs as follows. A carrier liquid bath may be deposited in the vessel to create a free surface for the creation or movement of CLCs. A CLC can then be created on or moved to the free surface and stabilized at a stabilization feature. The CLC can have the previously disclosed form in which a sample liquid is covered by an encapsulating liquid on the free surface of the carrier liquid, the three liquids all being mutually immiscible. The samples within the CLCs can then be processed by heating and/or cooling, i.e., thermocycling, the samples in a predetermined pattern, while possibly adding one or more reagents at a predetermined time or times in order to carry out a particular processing protocol. The plate, and consequently the CLCs, can be heated by activating the heating element or cooled by passing a cooling fluid through a cooling conduit. A cooling conduit can include both inlets and outlets for supplying and returning coolant. The entire process can be done without moving the CLCs from their stabilization features, and without removing sample liquid from any of the CLCs. Alternatively, the sample liquid may be removed from a CLC, or the entire CLC may be removed from the plate, during the procedure for some kind of off-plate processing. Off-plate processing could include, for example, isolating biomolecules in the sample liquid, for example, by use of magnetic beads. In general, the processing of the CLCs could include, for example, fragmentation and bar-coding, nucleic acid amplification by PCR or other methods, and/or observing electromagnetic radiation from a CLC in the vicinity of a stabilization feature to infer the presence of a target nucleic acid in the CLC's sample liquid.

As mentioned previously, the plate can be reusable, minimizing costly disposable elements. One method of reusing the plate involves removing the sample liquid and encapsulating liquid from any CLCs on the tray after processing. New CLCs can be formed by introducing new samples and encapsulating liquid on the free surface of the carrier liquid. The whole process can then be repeated with the new CLCs, processing the CLCs in place on their own stabilization features by heating, cooling and adding one or more reagents. The new CLCs need not be processed in the same manner as the first CLCs.

In another embodiment, the reusable plate is in the form of a PTFE disk containing 1440 CLC stabilizing features. The disk is mounted to a rotary actuator that allows it to rotate in increments of 2 degrees and sits in an aluminium bath containing carrier fluid. The period for each rotation increment can be modified for different incubation times required. The bath has an etched foil heater mounted to the underside of the aluminium. The heater is electrically connected to a controller, the controller being programmed to activate the heating element to generate a desired isothermal condition in the CLCs. Above the PTFE disk is an air layer approximately 10 mm thick. This air layer is insulated with a plastic cover over ¾ of the disk. The uncovered section is the operation zone where the CLCs are created and fluorescent detection occurs.

In another embodiment, the CLC stabilizing features in the plate include a region for the purpose of providing a relief path for any expanding air droplets trapped in the CLC. Without these features air droplets trapped at the oil interface may expand during thermal cycling and dispel the CLC out of the stabilizing feature. The air droplets will preferentially move into these relief paths instead of dispelling the CLC.

Integrated CLC Handling System

Figure 4:
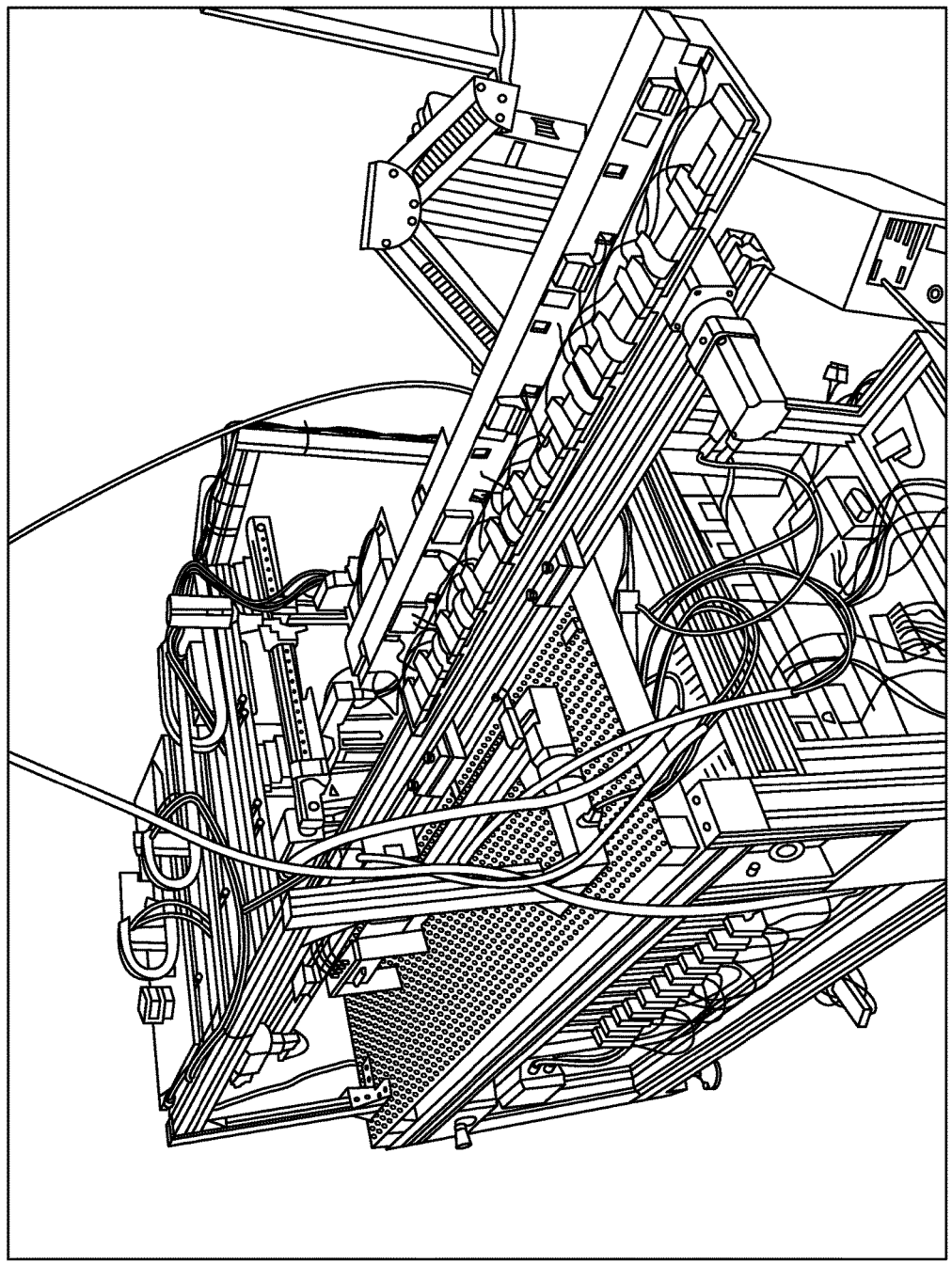
FIG. 4 is a photograph of an example of a full system.

A system for making and processing CLCs can include both the previously described capillary system, the reusable plate, and also a CLC forming system like the one described in detail in U.S. utility application Ser. No. 13/147,679, filed Aug. 3, 2011. As described in that earlier application which has been incorporated herein by reference, a CLC-forming system can include a sample-liquid input, an encapsulating-liquid input, a liquid-handling system, and a cell-forming controller operably connected to the liquid-handling system. The cell-forming controller can be programmed to cause the liquid handling system to (1) draw an encapsulating liquid from the encapsulating-liquid input, (2) discharge the drawn encapsulating liquid (a) onto a free surface of a carrier liquid in the vessel and (b) proximate to the stabilisation feature, the encapsulating liquid being immiscible with the carrier liquid, so that the discharged encapsulating liquid does not mix with the carrier liquid, floats on top of the carrier liquid, and is immobilised by the stabilisation feature, (3) draw a sample liquid from the sample-liquid input, and (4) discharge the drawn sample liquid, the sample liquid being immiscible with the encapsulating liquid and with the carrier liquid, so that the sample liquid does not mix with the encapsulating liquid or with the carrier liquid. In such a system, the capillary system and reusable plate can be located relative to one another so that the actuator is capable of moving the capillary tube to a dispensing location coincident with a stabilization feature. This will allow the capillary tube to dispense, for example, a reagent into an existing CLC, or to deposit sample material at a stabilization feature to create a CLC. Relatedly, the capillary system could simultaneously be the liquid handling system of the CLC-forming system. Likewise, the cell-forming controller and the capillary controller can be a single controller. An example can be seen in FIG. 4.

Alternatively, instead of the capillary dispensing system, any other metering system could be used instead. As an example, such a metering system could include a dispensing element, an actuator and a controller. The actuator can be configured to move the dispensing element to a desired location. The controller can be programmed to cause (1) the actuator to so move the dispensing element, (2) the dispensing element to draw liquid from a liquid input, and (3) the dispensing element to dispense liquid.

For example, such a system could be used to prepare DNA libraries for sequencing. Using the Ion Torrent Ampliseq chemistry as an exemplar, the process could proceed as follows:

(A) 10 96-node CLC chips are arrayed in a linear fashion and transported along a horizontal central axis of the system.

Figure 5:
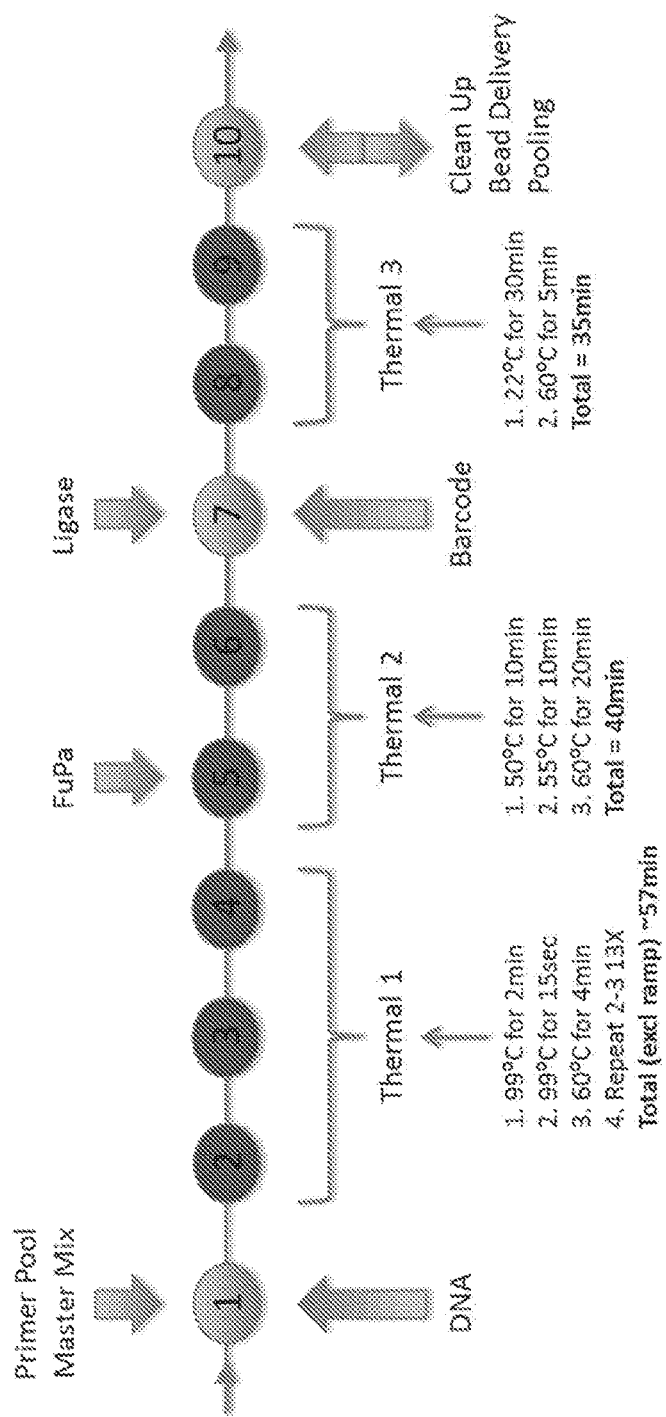
FIG. 5 schematically shows a particular protocol implemented on a full system.

(B) Along the central axis, addition/removal of reagents, thermal processing and DNA purification are carried out at a number of different stages. In this example, 10 stages are numbered 1-10 in FIG. 5. A stage where thermal processing occurs is denoted with a red background.

(C) CLC chip 1 is presented to stage 1, on the extreme left of the schematic. Here the chip remains stationary while DNA is transferred from microtitre source plates. Once the DNA has being transferred a reagent dispensing system (RDS) will dispense the primer pool and master mix according to the Ampliseq protocol.

(D) Once these three addition steps are completed CLC chip 1 will clock on to stage 2. Simultaneously CLC chip 2 is presented to stage 1.

(E) The stage 1 actions described above are now performed in CLC chip 2. Simultaneously, CLC chip 1 begins thermal process 1.

(F) Once the operations have completed at stages 1 & 2 the CLC chips clock on to the next station. CLC chip 1 is in stage 3, CLC chip 2 is in stage 2, CLC chip 3 is in stage 1.

(G) The remaining CLC chips are continually processed through the system where various operations are performed in parallel until all chips have passed through stage 10 on the extreme right of the schematic. At this point 960 unique DNA libraries have been created and pooled in pairs (1 pool=2 CLC chips=192 samples).

(H) The CLC chips are now reset and returned to the starting point of the instrument for the processing of further samples.

A further example is that of genotyping. In this protocol, the reusable plate is contained in a vessel or bath of carrier liquid. An etched foil heater electrically connected to a controller, the controller being programmed to activate the heating element to generate a desired isothermal condition in the CLCs. The plate containing mechanical stabilising features configured to stabilize a CLC on the free surface of the carrier liquid. The plate is of disk shape and is rotated in increments of 2 degrees. A CLC forming controller dispenses encapsulating liquid onto a free surface of the carrier liquid in the vessel. Following this, 7.5 ul of temperature specific chemistry is discharged into the CLC. Finally, 7.5 ul of the nucleic acid sample is added. The complete CLC undergoes incubation at the set temperature before undergoing fluorescent detection. Finally the sample is removed and the mechanical stabilisation feature is filled again with a CLC.

U.S. provisional application Ser. Nos. 61/344,434, filed Jul. 22, 2010, 61/470,515, filed Apr. 1, 2011, 61/470,520, filed Apr. 1, 2011, and 61/590,499, filed Jan. 25, 2012, and U.S. utility application Ser. No. 13/147,679, filed Aug. 3, 2011, are hereby incorporated herein by reference in their entirety.

We claim:

1. A capillary system comprising:
at least one capillary tube having an inner surface and an outer surface, the outer surface including an exterior wall of the capillary tube, a proximal end of the capillary tube and a distal end of the capillary tube, wherein:
the capillary tube has an internal diameter that is constant along the length of the capillary tube;
the outer surface of the capillary tube is substantially hydrophobic; and
the inner surface of the capillary tube includes:
a metering region that is substantially hydrophilic and adjacent to the distal end of the tube; and
a limiting region that is substantially hydrophobic, the limiting region being proximally adjacent to the metering region;
a pressure source in fluid communication with the proximal end of the capillary tube; and
a capillary controller operably connected to the pressure source, the capillary controller programmed to cause the pressure source to apply sufficient positive pressure to the proximal end of the capillary tube to drive an aqueous solution out of the distal end of the capillary tube;
wherein the capillary system further comprises an air sheath that applies an external air flow to the capillary tube.

2. The capillary system of claim 1 wherein the metering region comprises a substantially hydrophilic etched fluoropolymer and the limiting region and outer surface both comprise a substantially hydrophobic fluoropolymer.

3. The capillary system of claim 1 wherein the length and cross-sectional area of the metering region define a predetermined volume.

4. The capillary system of claim 1 wherein the capillary tube comprises a glass substrate.

5. The capillary system of claim 4 wherein the metering region comprises an exposed hydrophilic surface of the glass substrate.

6. The capillary system of claim 1 wherein:
the capillary tube comprises a glass substrate;
the metering region comprises an exposed hydrophilic surface of the glass substrate; and
the limiting region comprises a coated hydrophobic surface of the glass substrate.

7. The capillary system of claim 1 further comprising an actuator configured to move the capillary tube between locations, the actuator being operably connected to the capillary controller; and wherein the capillary controller is programmed to:
cause the actuator to move the capillary tube so that the distal end is in contact with an aqueous sample so that the aqueous sample is drawn into the metering region by capillary action;
cause the actuator to move the capillary tube to a dispensing location; and
cause the pressure source to apply sufficient positive pressure to the proximal end of the capillary tube to eject the aqueous sample from the distal end of the capillary tube.

8. The capillary system of claim 1 further wherein the capillary controller is further programmed to apply sufficient positive pressure to the proximal end of the capillary tube to stop capillary action in the metering region by balancing the capillary force with the force of the positive pressure.

9. The capillary system of claim 1 wherein the volume of the metering region is in the range of about 10 nanoliters to about 10000 nanoliters.

10. The capillary system of claim 1 further comprising a plurality of capillary tubes and a pressure conduit, wherein:
each of the plurality of capillary tubes has a distal end;
each distal end is in fluid communication with the pressure conduit; and
the pressure conduit is in fluid communication with the pressure source so that pressure applied from the pressure source is applied to all of the plurality of capillary tubes.

11. The capillary system of claim 1 wherein the internal diameter of the capillary tube ranges from 200 to 250 μm.

12. The capillary system of claim 1 wherein the volume of the metering region is 500 nanoliters.

* * * * *